(12) United States Patent
O'Lenick et al.

(10) Patent No.: US 7,786,241 B2
(45) Date of Patent: Aug. 31, 2010

(54) POLYESTER SILICONE RESINS

(76) Inventors: Kevin Anthony O'Lenick, 2170 Luke Edwards Rd., Dacula, GA (US) 30091; Anthony J. O'Lenick, Jr., 2170 Luke Edwards Rd., Dacula, GA (US) 30091

( * ) Notice: Subject to any disclaimer, the term of this patent is extended or adjusted under 35 U.S.C. 154(b) by 102 days.

(21) Appl. No.: 12/322,303

(22) Filed: Feb. 2, 2009

(65) Prior Publication Data

US 2010/0016501 A1    Jan. 21, 2010

Related U.S. Application Data

(60) Provisional application No. 61/134,948, filed on Jul. 16, 2008.

(51) Int. Cl.
*C08G 77/00* (2006.01)
*C08G 77/06* (2006.01)

(52) U.S. Cl. .......................... 528/41; 528/31

(58) Field of Classification Search .............. 528/10–45
See application file for complete search history.

(56) References Cited

U.S. PATENT DOCUMENTS 6,313,256 B1 * 11/2001 O'Lenick, Jr. ............... 528/28
6,388,042 B1 * 5/2002 O'Lenick, Jr. ............... 528/26
7,344,708 B1    3/2008 LaVay
7,361,721 B1    4/2008 O'Lenick
7,407,666 B2    8/2008 Tarletsky

FOREIGN PATENT DOCUMENTS

JP    2002212276 A  *  7/2002

OTHER PUBLICATIONS

English language machine translation of JP-2002-212276, 14 pages, machine translation generated on Jun. 15, 2010.*

* cited by examiner

*Primary Examiner*—Randy Gulakowski
*Assistant Examiner*—Robert Loewe

(57) ABSTRACT

The present invention is directed to a group of silicone polyesters and a process for making them by reacting a specific carboxy silicone and a hydroxy silicone to make a surprisingly organic soluble, more biodegradable film forming resin. Additionally, the invention discloses a process for applying pigment to a substrate including skin, metal or glass, which comprises contacting the skin with a dispersion of pigment, a volatile solvent, and the resin disclosed.

15 Claims, No Drawings

POLYESTER SILICONE RESINS

RELATED APPLICATIONS

This application claims priority to and benefit of U.S. Provisional Application No. 61/134,948 filed Jul. 16, 2008, the disclosure of which is incorporated herein for all purposes.

BACKGROUND OF THE INVENTION

Background of the Invention

The term silicone resin has been applied both to and misapplied to a variety of materials over time. Silicone resins as used herein refer to a series of products, which include at least two silicone backbones that are joined by a "crosslinking group". The number of crosslinking groups that are present as a percentage of the total molecular weight will determine the properties of the resulting polymer.

If there are no crosslinking groups; the polymer can freely rotate and consequently is an oily liquid. If a few crosslinking groups are introduced, the ability to rotate is slightly restricted and the oily material becomes "rubbery". The rubbery material should be referred to as an elastomer. The properties are more like a rubber band than plastic. As the percentage of crosslinking increases still the molecule becomes rigid. This class of compounds is a resins. If you hit the film with a hammer and it shatters it is a resin, if it bounces it is an elastomer and if it squirts out is a silicone fluid.

The difficulty in determining if a product is a fluid an elastomer or resin occurs for products that lie between the classifications. Specifically, when does an elastomer become a resin? While this exact point is of academic interest it does not have any practical significance to the present invention.

There are a number of classes of resin compounds differing in the nature of the crosslinker. One class is the so called "Q resins".

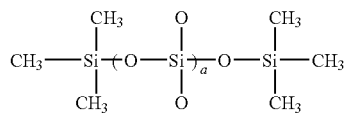

The oxygen that needs another bond connects to another polymer as shown:

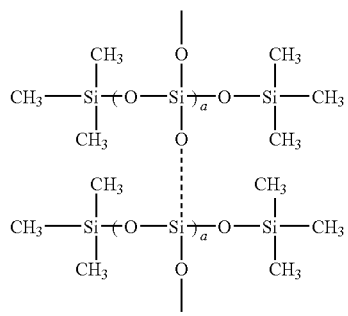

The crosslinking group is —O—. This type of resin is disclosed in U.S. Pat. No. 6,139,823, incorporated herein by reference. This type of material has a group, the so called "Q" group in which a Si has four oxygen atoms attached. In the above case it is the group that is within the "a" subscript. This type of resin is very powdery and is rarely used without a plasticizer. This class of compounds can also dry the skin.

The next class of resin contain alkyl connecting groups.

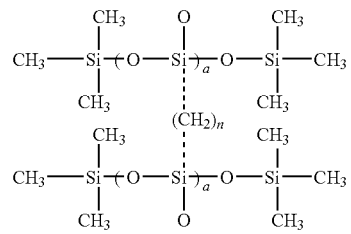

In the case where n=1 acetylene is used as a crosslinking reactant. It is reacted with a silanic hydrogen polymer. As n is increased the reactant is an alpha omega divinyl compound.

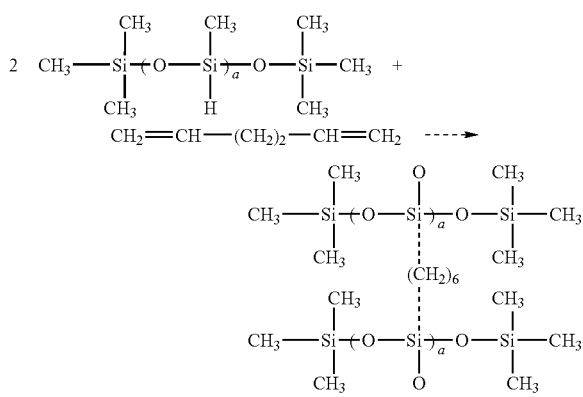

The reaction is called hydrosilylation and provides the linking groups between the molecules. The reaction is generally run in solvent like cyclomethicone (D4 or D5 or hexamethyl disiloxane) or in volatile organic like isododecane. A catalyst generally a platinum one is used to effect the reaction. Chloroplatinic acid or Karnsteadt catalyst are preferred. The resulting material is a viscous liquid that when the solvent evaporates provides a film.

The present invention is neither crosslinked nor the result of hydrosilylation technology. Despite the teaching s to the contrary, the silicone resins of the present invention are made by esterification of a linear hydroxy silicone and a linear silicon undecylente. This is done by introducing a C11 fatty ester linkage. Not only does this solubility change, the ability to formulate solid products free from syneresis also occurs. Another unexpected benefit is that the ester moiety provides improved biodegradation of the resin making the resin "more green" and improving consumer acceptability. None of these advantageous are present in the compounds known heretofore.

Silicone resins are known, but they do not have the fatty portion shown in the present invention as —O—C(O)—$(CH_2)_{10}$—. The presence of this fatty group makes the silicone resins of the present invention have more soluble in organic materials, rather than soluble in silicone materials. Of specific interest is the ability to make the resins of the present invention in esters and triglycerides, rather than cyclomethicone.

U.S. Patent Application 20070196309, incorporated herein by reference, discloses "Resins of the present invention are a class of silicone compounds which are prepared by the reaction of a di-vinyl silicone compound reacted with a terminal divinyl silanic hydrogen containing compound.

The terminal vinyl and terminal SiH on the same polymer chain eventually react with each other forming the chain. The length of the chain at which this backbiting occurs is solvent dependant. Larger molecular weight chains appear to form in hydrocarbon rather than in cyclomethicone solvents. While linear, these resins are made by the hydrosilylation and show that up until the present invention it was thought that hydrosilylation was the only method of making a resin.

U.S. Pat. No. 7,344,708 entitled Silicone polyester resins, incorporated herein by reference thaches a series of novel silicone polyesters which are prepared by crosslinking a dimethicone copolyol having at least 4 hydroxyl groups with a dimer acid. The ratio of acid groups to hydroxyl groups ranges from 0.7 to 1.4 so that a significant number of groups are reacted and a significant number of crosslink groups are achieved. This patent uses crosslinking, a feature lacking in the present materials.

The present invention also presents a series of more biodegradable polymers containing ester groups rather that the much more stable Si—C bonded materials of art. The resins of the present invention are made by classical methods (esterification) rather than silicone chemistry (hydrosilylation). The inclusion of a fatty soluble (dimer acid based) crosslinking reagent while resulting in a biodegradable ester containing destroys simultaneously destroys silicone solubility, by making the product oil soluble. The highly prized compound is one that has both a linear/linear structure and ester biodegradation.

The Invention

OBJECT OF THE INVENTION

The present invention is directed to a group of silicone polyesters.

Another objective is a process for making the silicone polyester of the present invention, which comprises reacting a specific carboxy silicone having 11 methylene groups and a hydroxy silicone to make a surprisingly organic soluble, more biodegradable film forming resin.

Another objective of the invention is a process for applying pigment to a substrate including skin, metal or glass, which comprises contacting the skin with a dispersion of pigment, a volatile solvent, and the resin of the present invention.

The resins of the current invention are useful in applications like paints, inks and coatings, and in cosmetics including but not limited to lipsticks, mascaras, transfer resistant lipsticks, powders and many other products in which silicone resins have been clearly shown to be effective.

SUMMARY OF THE INVENTION

The present invention is directed to a group of cyclic silicone polyesters and a process for making the silicone polyester of the present invention which comprises reacting a specific carboxy silicone having 11 methylene groups and a hydroxy silicone to make a surprisingly organic soluble, more biodegradable film forming resin.

The present invention is also directed to a process for applying pigment to a substrate including skin, metal or glass, which comprises contacting the skin with a dispersion of pigment, a volatile solvent, and the resin of the present invention.

DETAILED DESCRIPTION OF THE INVENTION

One aspect of the present invention relates to a series of resins that are polyester resins made by the esterification reaction of;
(a) a carboxy silicone compound conforming to the following structure:

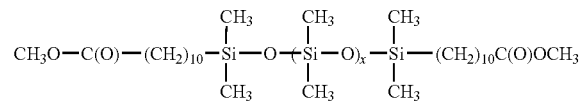

wherein:
  x is an integer ranging from 5 to 200;
with
b) a hydroxy silicone compound conforming to the following structure:

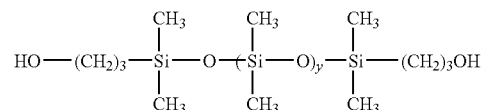

wherein:
  y is an integer ranging from 5 to 200.

In a preferred embodiment the esterification reaction is conducted at a temperature of between 150 and 200° C.

In a preferred embodiment the polyester is applied to skin, or hair.

In a more preferred embodiment the polyester applied to skin, or hair additionally contains pigment.

Another aspect of the present invention relates to a series of cyclic resins that are polyester resins made that conform to the following structure;

wherein
A is

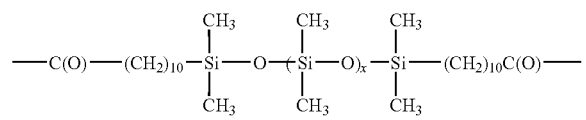

x is an integer ranging from 5 to 200;
B is:

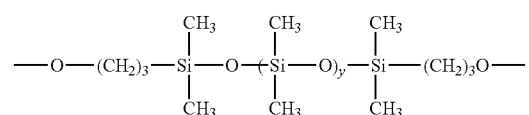

wherein:
  y is an integer ranging from 5 to 200.
  z is an integer ranging from 50 to 5,000.

In a preferred embodiment x is an integer ranging between 25 and 50.

In a preferred embodiment y is an integer ranging from 25 to 50.

In a preferred embodiment x is an integer ranging between 10 and 20.

In a preferred embodiment y is an integer ranging from 10 to 20.

In a preferred embodiment x is 50.

In a preferred embodiment y is 50.

We have also found that surprisingly that the resins forming the most flexible films are obtained when so-called homo-polymers are prepared. As used herein, the term homo-polymer means that the values of "x" and "y" are within a more narrow range relative to each other. Therefore the most preferred embodiment of the polymer is when both x and y are independently integers ranging between 25 and 50.

While not wanting to be bound by any specific theory the inventors believe that the construction of a homopolymers results in a polymer that is more likely to tail bite. Tail biting is the closing of ringed structures in which the carboxy containing portion of the polymer reacts with the hydroxy terminal group on the other end. This phenomenon results in resins and is strongly directed by the size of the molecule. Put another way there are certain distances that make tail biting more likely and ring closure more probable. The preferred embodiments shown below result in the most flexible films when applied to nonporous substrates like glass.

EXAMPLES

Hydroxy Functional Silicones

Hydroxy silicones are items of commerce sold by Siltech LLC Dacula, Ga. under the Silmer® OH trade name. They conforming to the following structure:

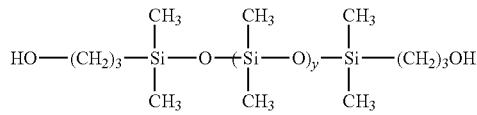

wherein:
y is an integer ranging from 5 to 200.

The values shown below were determined by Si29 nmr, not published trade literature.

| Example | y |
|---------|-----|
| 1 | 5 |
| 2 | 10 |
| 3 | 25 |
| 4 | 30 |
| 5 | 50 |
| 6 | 200 |

Carboxy Functional Silicones

Carboxy silicone compound conforming to the following structure:

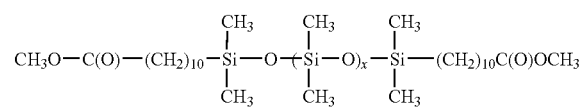

wherein:
x is an integer ranging from 5 to 200.

They are made by the hydrosilylation reaction of silanic hydrogen polymers conforming to the following structure:

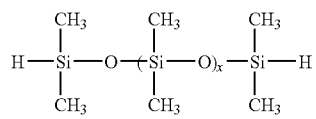

wherein:
x is an integer ranging from 5 to 200.
with methyl undecylenate, a compound conforming to the following structure:

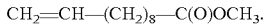

$CH_2=CH-(CH_2)_8-C(O)OCH_3$.

Preparation of Undecylenate Intermediates

Silanic Hydrogen Raw Materials

Silanic Hydrogen compounds are known materials available from several sources including Siltech LLC Dacula, Ga. They conform to the following structure:

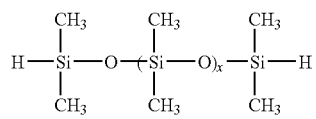

wherein:
x is an integer ranging from 5 to 200.

The values shown below were determined by Si29 NMR, not published trade literature.

| Example | x |
|---------|-----|
| 7 | 5 |
| 8 | 10 |
| 9 | 25 |
| 10 | 30 |
| 11 | 50 |
| 12 | 200 |

Reaction Sequence

Hydrosilylation reactions are known and are shown in the reaction below:

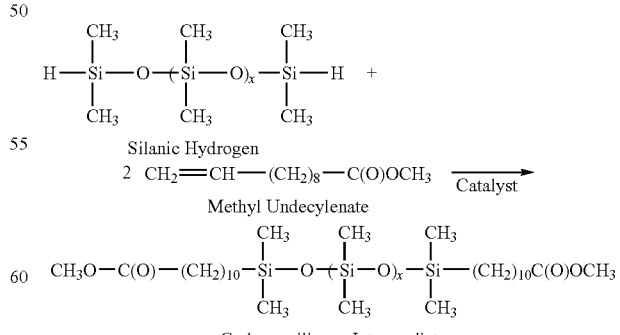

General Procedure

The specified number of grams of the specified Silanic Hydrogen intermediate (Examples 7-12) is added to 500.0 grams of methyl undecylenate. The reaction is blanketed under nitrogen heated to 80° C. Next add 500 ppm (parts per million) of Karnstedt catalyst (based upon the total weight of methyl undecylenate and silanic hydrogen compound). An exotherm will result bringing the temperature to 100° C. Keep the temperature at between 100° C. and 120° C. for 2 hours. Any excess methyl undecylenate is removed using vacuum.

The product is used without additional purification.

Non Homopolymers

|  | Silanic Hydrogen | |
|---|---|---|
| Example | Example | Grams |
| 13 | 7 | 506.0 |
| 14 | 8 | 876.0 |
| 15 | 9 | 1986.0 |
| 16 | 10 | 2356.0 |
| 17 | 11 | 3836.0 |
| 18 | 12 | 14936.0 |

Compounds of the Present Invention

General Procedure

To a reaction flask equipped with agitation, heat and a distillation is added the specified number of grams of the specified carboxy silicone is added the specified number of grams of the specified hydroxy silicone. Next is added 0.1% by weight of stannous oxylate (based upon the combined weight of the carboxy and hydroxy silicones). The heat is turned on and the reaction mass is heated to 200° C. Methanol is distilled off. Once the amount of methanol approaches 95% of theoretical the mass will get very thick. Allow to cool.

The resulting product is diluted with isododecane to between 50% by weight of polymer.

The range of dilution can be between 20% and 60% by weight of polymer but 50% by eight of polymer is preferred. The dilution will cut the viscosity and the product will be easily flowable. Suitable other solvents include D5 (cyclopentasiloxane) and a variety of esters including triglycerides and natural oils.

Preferred Homopolymers

In a preferred embodiment x and y are both between 25 and 50.

|  | Carboxy Silicones | | Hydroxy Silicones | |
|---|---|---|---|---|
| Example | Example | Grams | Example | Grams |
| 19 | 15 | 2383.0 | 3 | 2102.0 |
| 20 | 16 | 2752.0 | 4 | 2472.0 |
| 21 | 17 | 4232.0 | 5 | 3952.0 |
| 22 | 15 | 2383.0 | 5 | 3952.0 |
| 23 | 16 | 2752.0 | 3 | 2102.0 |
| 24 | 17 | 4232.0 | 4 | 2472.0 |

Less Preferred Non-Homopolymers

|  | Carboxy Silicones | | Hydroxy Silicones | |
|---|---|---|---|---|
| Example | Example | Grams | Example | Grams |
| 25 | 15 | 2383.0 | 1 | 622.0 |
| 26 | 16 | 2752.0 | 2 | 992.0 |
| 27 | 17 | 4232.0 | 6 | 15502.0 |
| 28 | 13 | 902.0 | 1 | 622.0 |
| 29 | 14 | 1272.0 | 2 | 992.0 |
| 30 | 13 | 902.0 | 6 | 15052.0 |

Applications Examples

The compounds (examples 19-30) were evaluated at 50% solids in isododecane. 2 grams of product were placed on glass plated and allowed to dry overnight. The resulting film was evaluated on a scale of 0-5 (with 5 being best, 0 being worst). The Ability to form a film on dry down was evaluated as well as the ability to pull the film off the glass without breaking again using a scale of 0-5 (with 5 being best, 0 being worst). The results are shown below.

Preferred

| Example | Film Formation | Flexibility |
|---|---|---|
| 19 | 5 | 5 |
| 20 | 4 | 5 |
| 21 | 5 | 4 |
| 22 | 5 | 5 |
| 23 | 4 | 4 |
| 24 | 4 | 4 |

Less Preferred

| Example | Film Formation | Flexibility |
|---|---|---|
| 25 | 3 | 3 |
| 26 | 3 | 3 |
| 27 | 2 | 3 |
| 28 | 3 | 3 |
| 29 | 2 | 3 |
| 30 | 2 | 3 |

As can readily be seen the compounds of the current invention are good flexible film forming polymers that have flexibility. The preferred embodiment polymers (that is when x and y are both between 25 and 50) are outstanding products.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A silicone polyester made by the esterification reaction of;

(a) a carboxy silicone compound conforming to the following structure:

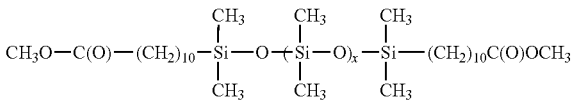

wherein:
x is an integer ranging from 5 to 200;
with b) a hydroxy silicone compound conforming to the following structure:

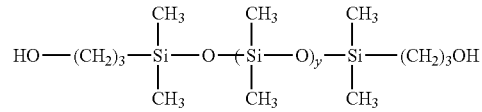

wherein:
  y is an integer ranging from 5 to 200.

2. A polyester silicone of claim 1 wherein said esterification reaction is conducted at a temperature of between 150 and 200° C.

3. A polyester silicone of claim 1 wherein x is an integer ranging between 25 and 50.

4. A polyester silicone of claim 1 wherein y is an integer ranging from 25 to 50.

5. A polyester silicone of claim 1 wherein both x and y are independently integers ranging from 25 to 50.

6. A polyester silicone of claim 1 wherein x is an integer ranging between 10 and 20.

7. A polyester silicone of claim 1 wherein y is an integer ranging from 10 to 20.

8. A polyester silicone of claim 1 applied to skin, or hair.

9. A polyester silicone of claim 8 additionally containing pigment.

10. A silicone polyester conforming to the following structure;

wherein
A is

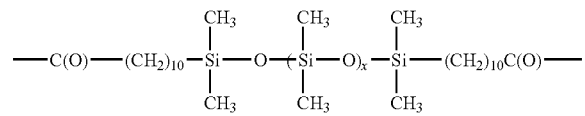

x is an integer ranging from 5 to 200;

B is:

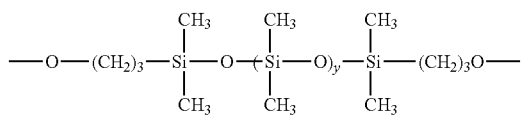

wherein:
  y is an integer ranging from 5 to 200;
  z is an integer ranging from 50 to 5,000.

11. A polyester silicone of claim 10 wherein x is an integer ranging between 25 and 50.

12. A polyester silicone of claim 10 wherein y is an integer ranging from 25 to 50.

13. A polyester silicone of claim 10 wherein both x and y are independently integers ranging from 25 to 50.

14. A polyester silicone of claim 10 wherein x is an integer ranging between 10 and 20.

15. A polyester silicone of claim 10 wherein y is an integer ranging from 10 to 20.

* * * * *